US00PP15065P2

(12) United States Plant Patent
Broyles, Jr.

(10) Patent No.: US PP15,065 P2
(45) Date of Patent: Aug. 3, 2004

(54) DRACAENA PLANT NAMED 'TARZAN'

(50) Latin Name: *Dracaena marginata*
Varietal Denomination: Tarzan

(75) Inventor: Donald E. Broyles, Jr., Homestead, FL (US)

(73) Assignee: Sunshine Tropical Foliage, Inc., Homestead, FL (US)

( * ) Notice: Subject to any disclaimer, the term of this patent is extended or adjusted under 35 U.S.C. 154(b) by 0 days.

(21) Appl. No.: 10/716,015

(22) Filed: Nov. 18, 2003

(51) Int. Cl.[7] ..... A01H 5/00
(52) U.S. Cl. ..... Plt./383
(58) Field of Search ..... Plt./383

*Primary Examiner*—Anne Marie Grunberg
*Assistant Examiner*—Annette H Para
(74) *Attorney, Agent, or Firm*—C. A. Whealy

(57) ABSTRACT

A distinct cultivar of Dracaena plant named 'Tarzan', characterized by its upright growth habit; slender stems; linear and fleshy leaves that are glossy dark green in color with dark purple-colored margins; and excellent keeping quality.

2 Drawing Sheets

Botanical classification/cultivar designation: *Dracaena marginata* cultivar Tarzan.

BACKGROUND OF THE INVENTION

The present invention relates to a new and distinct cultivar of Dracaena plant, botanically known as *Dracaena marginata,* and hereinafter referred to by the cultivar name Tarzan.

The new cultivar was discovered by the Inventor in a controlled environment in Homestead, Fla. in 1998 as a naturally-occurring whole plant mutation of an unidentified selection of *Dracaena marginata,* not patented. The new Dracaena was observed by the Inventor as a single plant within a large population of plants of the unidentified *Dracaena marginata* selection.

Asexual propagation of the new cultivar by cuttings at Homestead, Fla. since 1998, has shown that the unique features of this new Dracaena plant are stable and reproduced true to type in successive generations of asexual propagation.

SUMMARY OF THE INVENTION

The new Dracaena has not been observed under all possible environmental conditions. The phenotype may vary somewhat with variations in environment such as temperature and light intensity, without, however, any variance in genotype. The following traits have been repeatedly observed and are determined to be the unique characteristics of 'Tarzan'. These characteristics in combination distinguish 'Tarzan' as a new and distinct cultivar:

1. Upright growth habit.
2. Slender stems.
3. Linear and fleshy leaves that are glossy dark green in color with dark purple-colored margins.
4. Excellent keeping quality; durable.

Plants of the new Dracaena can be compared to plants of the parent selection and other selections of *Dracaena marginata* known to the Inventor. In side-by-side comparisons conducted in Homestead, Fla., plants of the new Dracaena differed from plants of the parent selection and other known selections of *Dracaena marginata* in the following characteristics:

1. Plants of the new Dracaena grew more slowly than plants of the parent selection and other known selections of *Dracaena marginata.*
2. Plants of the new Dracaena had more leaves and were denser and bushier than plants of the parent selection and other known selections of *Dracaena marginata.*
3. Plants of the new Dracaena had narrower stems than plants of the parent selection and other known selections of *Dracaena marginata.*
4. Plants of the new Dracaena had longer and broader leaves than plants of the parent selection and other known selections of *Dracaena marginata.*
5. Plants of the new Dracaena were most resistant to pests common to Dracaenas than plants of the parent selection and other known selections of *Dracaena marginata.*

DESCRIPTION OF THE PHOTOGRAPHS

The accompanying colored photographs illustrate the overall appearance of the new cultivar, showing the colors as true as it is reasonably possible to obtain in colored reproductions of this type. Colors in the photographs may differ slightly from the color values cited in the detailed botanical description which accurately describe the actual colors of the new Dracaena.

The photograph on the first sheet comprises a side perspective view of a typical plant of 'Tarzan'.

The photograph on the second sheet is a close-up view of typical leaves of 'Tarzan'.

DETAILED BOTANICAL DESCRIPTION

The aforementioned photographs and following observations and measurements describe three-year old plants grown in Homestead, Fla. in an outdoor nursery. During the production of the plants, day temperatures ranged from 12 to 33° C. and night temperatures ranged from 4 to 24° C. In the description, color references are made to The Royal Horticultural Society Colour Chart, 1995 Edition, except where general terms of ordinary dictionary significance are used.

Botanical classification: *Dracaena marginata* cultivar Tarzan.

Parentage: Naturally-occurring whole plant mutation of an unidentified selection of *Dracaena marginata,* not patented.

Propagation:

*Method.*—By cuttings.

*Time to produce a rooted plant.*—Summer: About 90 days at 26° C. Winter: About 120 days at 23° C.

*Root description.*—Numerous, dense; thick; tan in color.

Plant description:

*Plant shape.*—Upright plant habit.

*Plant height.*—About 108 cm.

*Plant diameter or spread.*—About 62 cm.

*Plant vigor.*—Moderate.

*Growth rate.*—Relatively slow.

*Stem diameter, at base.*—About 2.3 cm; slender.

*Stem color.*—Close to 199B.

*Foliage description.*—Relatively long and broad; mostly erect; decurrent, sessile. Quantity of leaves per finished plant: About 78; bushy and dense. Arrangement: Whorled. Shape: Linear. Apex: Sharply acute. Margin: Entire. Texture, upper and lower surfaces: Leathery, fleshy; smooth, glabrous. Luster, upper and lower surfaces: Glossy. Venation pattern: Parallel. Length: About 53 cm. Width, at broadest point: About 3.9 cm. Color: Developing and fully expanded leaves, upper surface: Close to 147A; narrow margin, close to 187A. Developing and fully expanded leaves, lower surface: Darker green than 146A; narrow margin, close to 187A. Midrib, upper surface: Close to 146A. Midrib, lower surface: Between 144A and 146A. Lateral veins, upper and lower surfaces: Same as lamina coloration.

Flower description: Flowers have not been observed on plants of the new Dracaena.

Keeping quality: Plants of the new Dracaena are durable and will maintain good leaf substance indefinitely under interior conditions.

Disease/pest resistance: Under commercial conditions, resistance to pathogens common to Dracaenas has not been observed. Compared to the parent selection and other selections of *Dracaena marginata* known to the Inventor, plants of the new Dracaena are more resistant to Spider Mites, Mealybugs and Scale.

Temperature tolerance: Plants of the new Dracaena have been observed to tolerate temperatures from 2 to 36° C.

It is claimed:

1. A new and distinct cultivar of Dracaena plant named 'Tarzan' as illustrated and described.

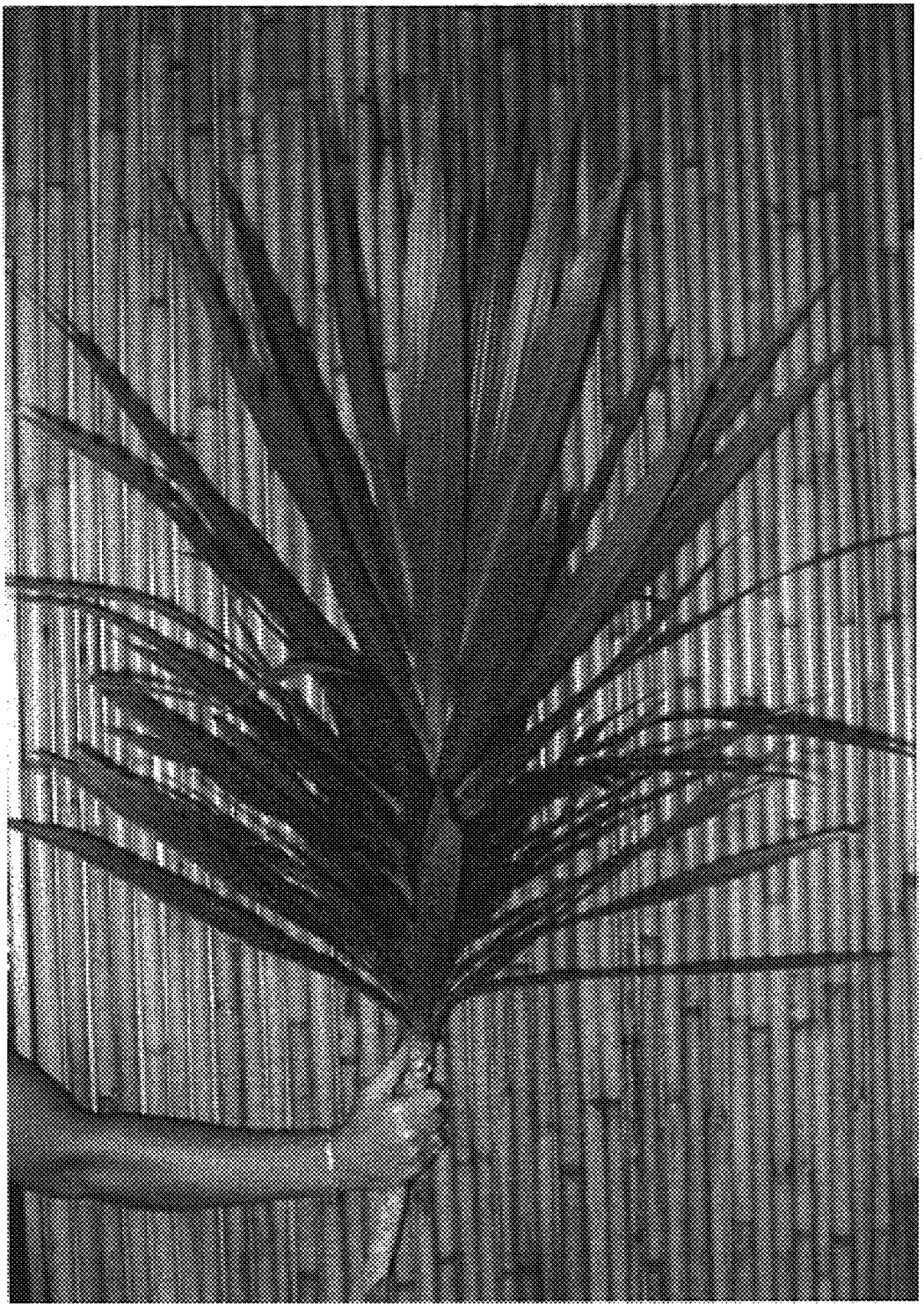

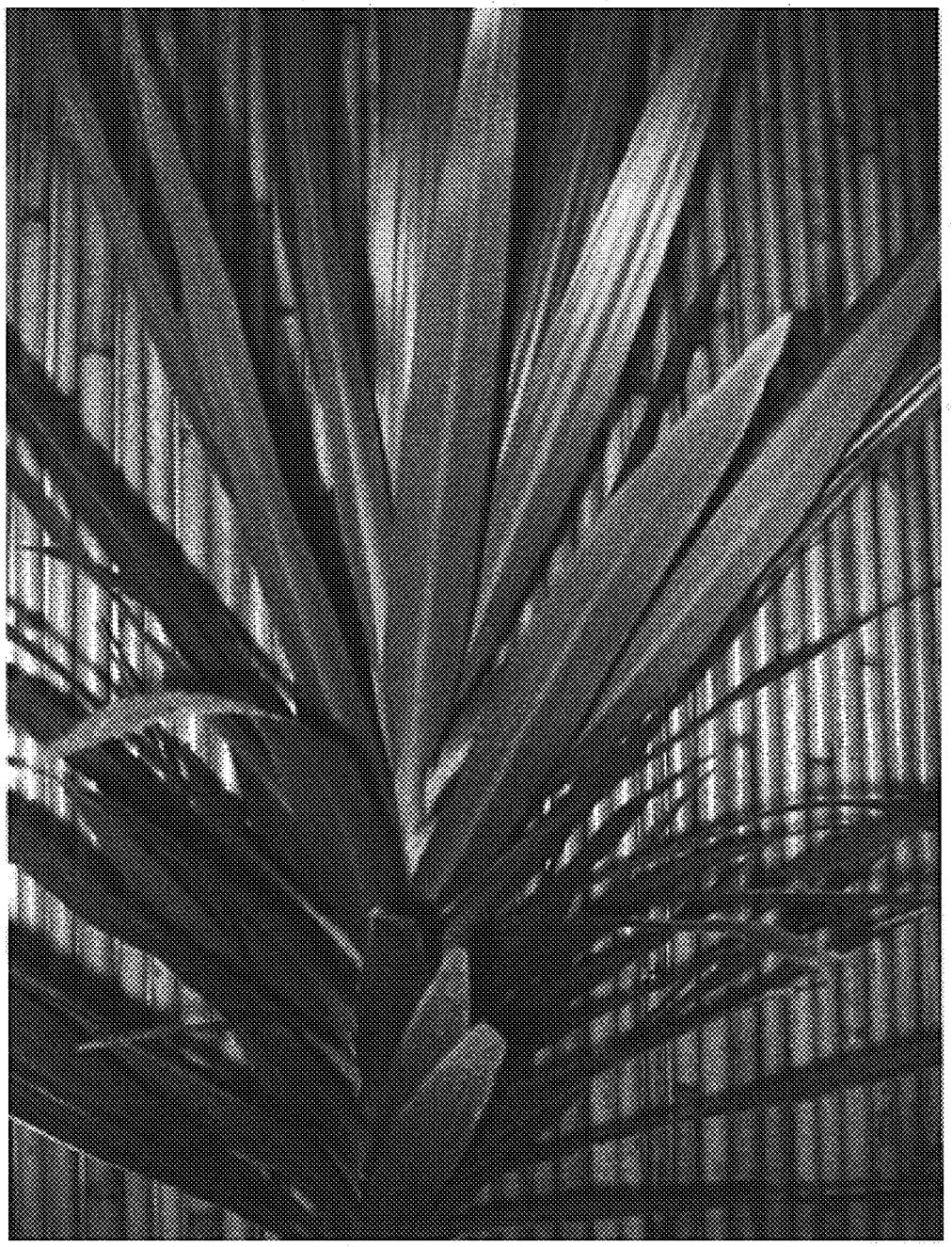

* * * * *